(12) United States Patent
Maciejewski

(10) Patent No.: US 7,516,501 B2
(45) Date of Patent: Apr. 14, 2009

(54) MEDICAL DEVICE

(75) Inventor: Bernd Maciejewski, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/986,860

(22) Filed: Nov. 27, 2007

(65) Prior Publication Data

US 2008/0134433 A1    Jun. 12, 2008

(30) Foreign Application Priority Data

Dec. 8, 2006    (DE) .................. 10 2006 057 985

(51) Int. Cl.
*A61G 7/00*    (2006.01)
*A61G 13/00*    (2006.01)

(52) U.S. Cl. .................... 5/601; 5/424; 5/943; 378/209

(58) Field of Classification Search .................... 5/601, 5/424, 600, 943; 378/209; 600/415
See application file for complete search history.

(56) References Cited

U.S. PATENT DOCUMENTS 5,600,858 A * 2/1997 Baer .............................. 5/601

2005/0204472 A1    9/2005 Gagneur et al.

FOREIGN PATENT DOCUMENTS

| DE | 10160802 A1 | 6/2003 |
|---|---|---|
| DE | 102004052265 A1 | 7/2005 |
| JP | 2000110416 A | 4/2000 |
| JP | 2002213112 A | 7/2002 |

* cited by examiner

*Primary Examiner*—Alexander Grosz

(57) ABSTRACT

Medical device with a patient tunnel lined by a lining and a patient couch that can be moved into and out of the tunnel and accommodated in a recess in the lining enclosing the sides of the patient couch, with the patient couch having a clearance from the lining when fully withdrawn from the tunnel, with an element that can be moved against a resetting force being provided at both sides in each case in the area of the recess near to the couch, it being possible for said element during a vertical movement from a lowered position into the completely withdrawn position or at the start of the inward movement to be deflected by the patient couch against the resetting force to a position separated from the patient couch by a narrow gap or to a position abutting against the patient couch.

18 Claims, 4 Drawing Sheets

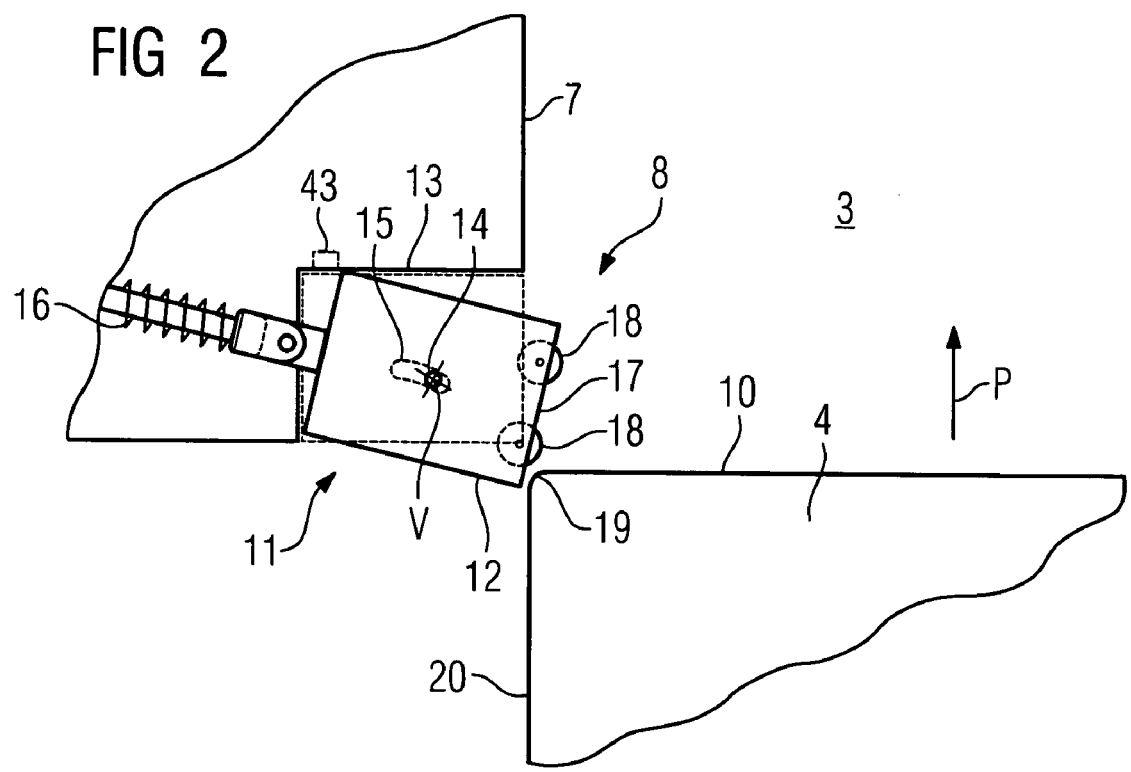
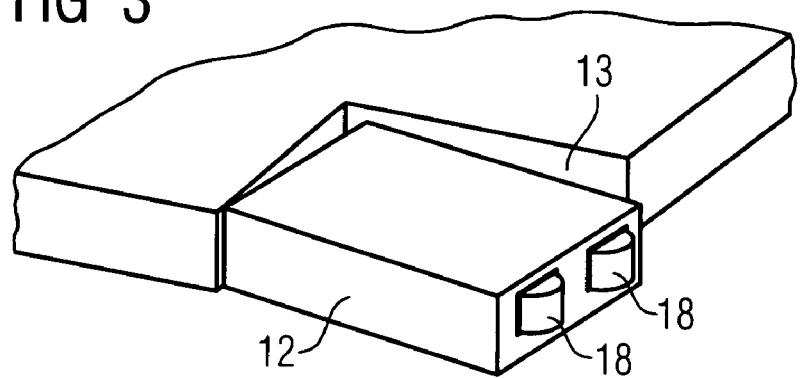

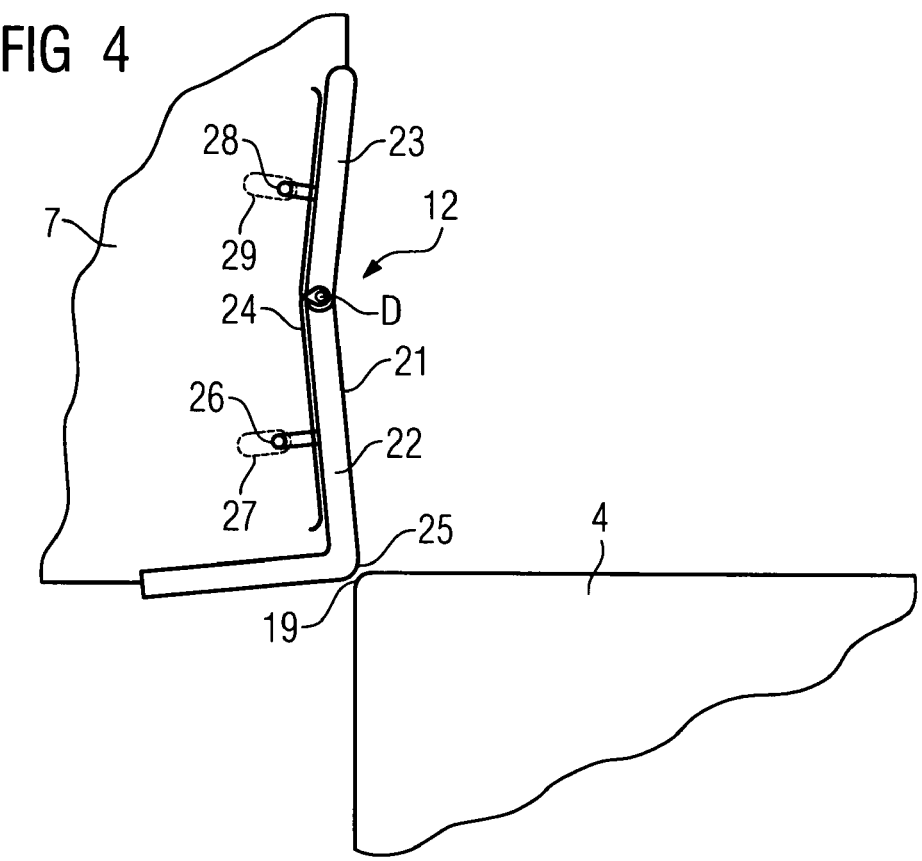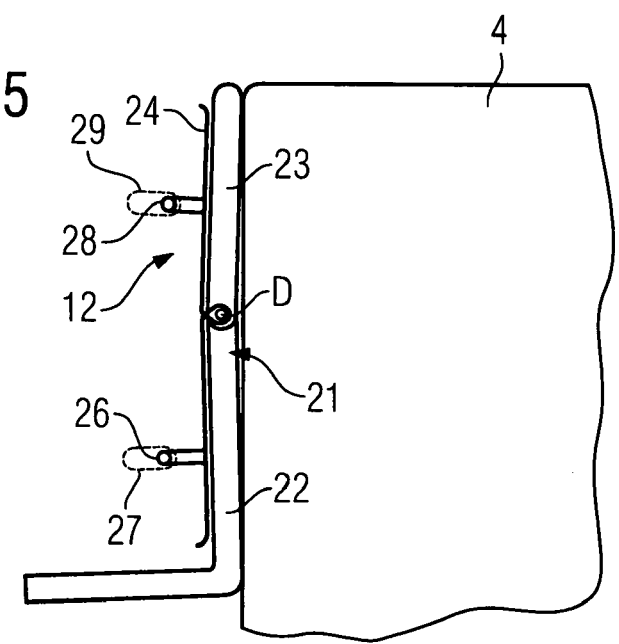

MEDICAL DEVICE

CROSS REFERENCE TO RELATED APPLICATIONS

This application claims priority of German application No. 10 2006 057 985.2 filed Dec. 8, 2006, which is incorporated by reference herein in its entirety.

FIELD OF THE INVENTION

The invention relates to a medical device with a lined patient tunnel and a patient couch that can be moved in and out of the tunnel and accommodated in a recess in the lining surrounding the sides of the patient couch, with the patient couch moved out of the tunnel in the withdrawn position and having a clearance from the lining.

BACKGROUND OF THE INVENTION

Known medical devices, such as magnetic resonance devices, have a patient couch that is vertically moveable so that it can be lowered to make it easy for the patient to climb on and off. The raised patient couch can also be moved horizontally and can be moved into the patient tunnel. During this inward and outward movement, the patient couch is accommodated at the sides in corresponding recesses in the inner lining of the patient tunnel.

It is obvious that it must be possible to completely withdraw the patient couch from the patient tunnel, and therefore from the recess, in order to lower it. In the completely withdrawn position, the front edge of the patient couch has a clearance of a few millimeters from the lining. When being moved in, the front edge or the front corner sections of the patient couch are inserted into the recess in the lining. There is necessarily a gap here between the sides of the patient couch and the lining in the area of the recess, as viewed from the front of the magnetic resonance device, i.e. viewed in the horizontal direction, there is always a narrow gap between the sides of the patient couch and the recess in the lining. This gap is problematic in that a finger or the skin of the patient can enter into this gap during the inward movement, so that crushing or grazing can occur. Frequently the hands of the patient are not on the top on the couch but instead slid slightly to the side so that a finger can be in the area of the sides of the couch. With elderly or corpulent patients it is possible for part of the body to overhang the sides of the couch. In both cases it is possible during the inward movement for a finger laid at the side or an overhanging part of the skin to get caught in the gap open toward the front, possibly causing painful crushing or grazing etc.

SUMMARY OF THE INVENTION

The object of the invention is to provide a medical device that reduces the danger of such trapping.

To achieve this object, according to the invention it is provided that in the case of a medical device of the type referred to in the introduction an element that can be moved against a resetting force is provided at both sides in the area of the end of the recess next to the couch, it being possible for said element during a vertical movement from a lowered position into the completely withdrawn position or at the start of the inward movement to be deflected by the patient couch against the resetting force to a position separated from the patient couch by a narrow gap or to a position abutting against the patient couch.

With the medical device according to the invention, corresponding closure elements are provided on the lining at both sides of the couch, and can be actuated by the patient couch depending on the direction of movement and by means of which it is possible to clearly reduce the relatively large gap (up to 8 mm) that otherwise would exist, or for them to slide against a patient couch immediately they are actuated by the patient couch, so that then there would be no gap in which fingers or flaps of skin could be crushed. In this case both elements are in an at-rest position, so to speak, when the patient couch is withdrawn or lowered and can only be moved from this position by the patient couch and brought to a working position in which, as stated, they abut the sides of the patient couch very closely. After both elements have been actuated by the patient couch either during a vertical movement into the completely withdrawn position or immediately before the start of the inward movement, the previously wide gap is narrowed or closed as soon as the danger exists that a finger or flap of skin etc. could enter the gap, regardless of whether the patient is moved in head first or feet first. The closure of the gap always takes place while parts of the patient's body are still far from this gap. Consequently, very effective protection against trapping is realized which, because it is activated by the patient couch alone and is moved thereto by the patient couch, also enables a simple insertion of the patient couch into the lining recess, which thus can still be open sufficiently wide at the front of the lining.

A closure element that is swivel mounted is particularly preferred and therefore can be moved between an at-rest position, in which the patient couch is completely withdrawn from the lining or recess, and a closed swung-in position.

Different embodiments are conceivable in this case. According to a first inventive alternative, an element can be designed as a sliding bearing component that swivels about a vertical axis. This sliding bearing component can be any geometrical element that can be moved between the at-rest position and the closed position by means of a suitable resetting force, for example a coil spring. In the closed position, the two sliding bearing components lie touching the sides of the patient couch and thus slide along said patient couch when the couch is being moved into, or out of, the tunnel. To enable sliding that is as friction-free as possible, each sliding bearing part can have one or more rollers on the side that engage on the patient couch or be provided with a sliding covering, or be constructed using material that has good sliding properties, such as Teflon.

Both sliding bearing components, that can swivel about a vertical axes, are preferably arranged so that in the at-rest position their inlet surfaces, against which the patient couch runs to swing into the closed position, are arranged sloping at an angle that opens out relative to the longitudinal axis of the patient couch and lie essentially parallel to the longitudinal axis in the swung-in position. Both sliding bearing components therefore open outwards, so to speak, so that a sort of inlet funnel results and ensures that the patient couch can be safely inserted. Immediately both side edges of the patient couch strike the inlet surfaces, the sliding bearing components are partially swung inward to the sides of the couch to make a sliding contact with said couch sides.

As an alternative to the design as sliding bearing components, for example in the form of pad-type closure pieces or similar, the closure elements can also be designed as swivel levers, each of which can swivel about a vertical axis. These swivel levers also can be moved by the patient couch from the at-rest position to the closed position, with the swivel levers in this embodiment of the invention being swung somewhat further inward, for example in the at-rest position, and moved outward by the patient couch moving against them, and in sliding manner abutting the sides of the patient couch in the closed position. In this case also the swivel levers can have suitable sliding coverings or similar. To ensure a secure swiveling movement when the patient couch runs against them, each swivel lever appropriately has a rounded striking edge for the patient couch. This striking edge should have the smallest possible radius so that no additional trapping gap or similar results in the transition area from the edge of the swivel lever to the patient couch.

According to a first alternative, the swivel lever itself can be a single-part component and therefore can consequently be swivel mounted at one end and preloaded by a spring. It is also conceivable for the swivel lever to be of two-part design so that it has a first front lever section and second rear lever section, both of which can be swiveled against a resetting force about a common axis of rotation.

In principle, the swivel lever can preferably be coupled with a leaf spring that generates the resetting force, with the resetting force being applied if necessary to both sections of the lever. If the swivel lever is of two-part design, each lever section serves as a sliding element, i.e. each lever section abuts against the patient couch and closes the gap when said patient couch is pushed in sufficiently.

It is also conceivable to provide a further, especially swiveling, separate lever section on the swivel lever, possibly on the front section of the lever, at the end near to the couch, with said further lever section being moveable against a further, preferably smaller resetting force and being the first to be contacted by the patient couch. This very short lever section is very easy to swivel and can very quickly and precisely adapt to the couch. With a two-part swivel lever, three separate lever sections are then finally provided with this embodiment, with the sections being moved, like links, in succession by the patient couch and abutting against said couch. The extra lever section is also preferably preloaded by means of a leaf spring with a lower resetting force.

Finally, one element can also be swivelable about a horizontal axis and have a pickup section that can be engaged underneath by the top of the respective edge of the couch. With this embodiment, the element is moved from the at-rest position to the closed position during a vertical movement of the couch from a lower position to the raised fully withdrawn position. In doing so the edges of the couch move against the pickup sections of the horizontally swiveling elements, so that these are moved upwards. These either snap into a closed position in which they have a minimum gap (the "narrow gap" within the meaning of the definition given in the introduction is preferably approximately 2 mm or less) relative to the couch, or they abut against the couch in sliding fashion, preferably with a suitable sliding covering. The element in this case is preferably designed in the form of a clamp so that it engages over the edge of the couch at the top, sides and underside.

If the element that can swivel about a horizontal axis is not locked in the closed position, it is pushed downward into the at-rest position again by the resetting force, in this case preferably also a coil spring, when the patient couch has moved so far into the tunnel that the rear end of the couch has again moved out of the elements. So that the couch can be re-inserted into the elements when moving back, each element preferably has a pickup bevel on the rear end by means of which the element can, when the patient couch moves back, be gripped and moved from the at-rest position to the swung-in position by the patient couch which is moved fully into the patient tunnel and does not engage with the element.

A further useful embodiment of the invention provides that one or both elements each has a sensor for detecting an impermissibly high force acting on the element or an impermissible element position, with the sensor communicating with a control device controlling the movement of the couch. If for any reason a finger or flap of skin or similar nevertheless enters the gap, this can be detected immediately by the sensor and the couch stopped immediately. Because ultimately this is possible only if the patient couch has still not engaged with the elements, since only then is there still a sufficiently large gap into which a finger or similar can be inserted, this hazard situation can only occur if the couch is still completely withdrawn from the recess, i.e. directly at the start of the horizontal inward movement. If then a patient with hands outstretched forward grips the edges of the couch and enters into the gap area, this is immediately detected because an impermissibly high pressure would be exerted on the element due to the gripping fingers, and/or the element would be brought to a position not reached in normal operation, so that the patient couch, still moving extremely slowly in this case, would be stopped immediately by an emergency shutdown action.

BRIEF DESCRIPTION OF THE DRAWINGS

Further advantages, features and details of the invention are given in the exemplary embodiments described in the following, with the aid of drawings. The drawings are as follows:

FIG. 2 A plan view showing a schematic representation of a first embodiment of a closure element, FIG. 3 A front elevation of the arrangement in FIG. 2, FIG. 4 A second embodiment of an inventive closure element, FIG. 5 The arrangement from FIG. 4 showing the patient couch moved in, FIG. 6 A third embodiment of an inventive closure element, FIG. 7 A fourth embodiment of a vertically actuated inventive closure element, FIG. 8 The arrangement from FIG. 7 showing the patient couch raised, and FIG. 9 A representation of the closure element from FIG. 7, showing a pick-up bevel.

DETAILED DESCRIPTION OF THE INVENTION

Figure 1:
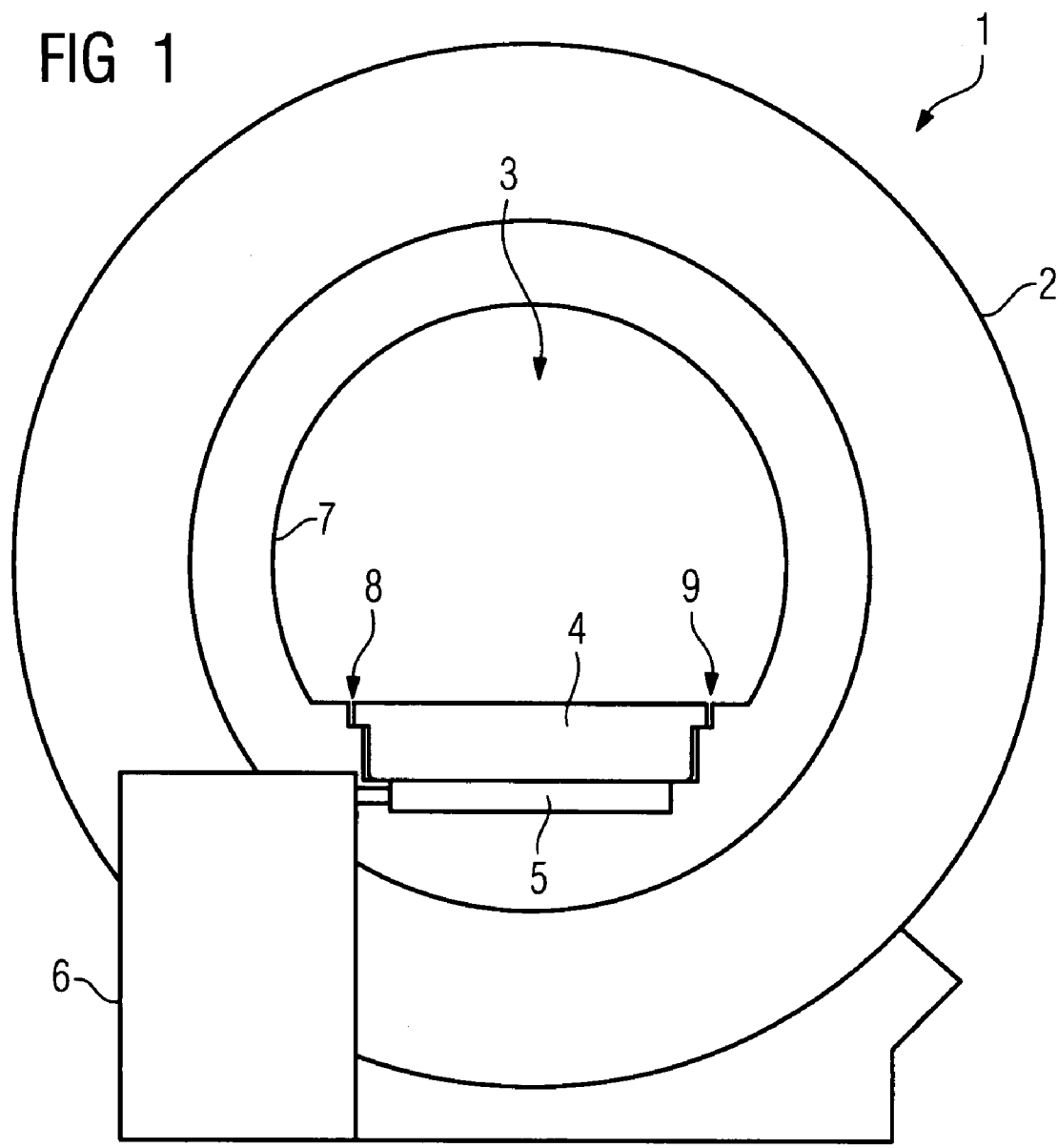
FIG. 1 A schematic representation of an inventive magnetic resonance unit.

FIG. 1 shows an inventive magnetic resonance device 1, consisting of the actual magnetic resonance part 2 with a patient tunnel 3 and a patient couch 4, carried on a horizontally movable carrier arm 5 that is in turn arranged on a lifting frame 6. The patient tunnel 3 is lined by an inner lining 7 that merges into a front lining. A recess 8, the contour of which essentially corresponds to the side contour of the patient couch 4, is provided in the inner lining 7. For simplicity, the recess 8 in this case is shown stepped on both sides, with the patient couch 4 also being stepped at the side. A problem during the inward movement is the gap 9 that occurs between the side of the patient couch 4 and the side surfaces of the recess 8, into which, if no inventive protective mechanism is provided, a finger or similar can become trapped.

A first embodiment of a protective mechanism of this kind is shown in FIG. 2. The illustration shows a plan view of the recess 8 and the front edge 10 of the patient couch 4 leading to the patient tunnel 3. The patient couch 4 is not yet moved into the recess and is in fact a few millimeters from this in a completely withdrawn position in which it can also be moved vertically. At the end 11 of the recess 8 near to the couch, i.e. immediately in the area of the vertical front lining, an element 12 that serves to close the gap 9 is provided on both sides of the recess 8. The element 12 in this case is in the form of a pad or block and, for example, has a height of few centimeters, e.g. 2 cm, with a length and width also of a few centimeters, e.g. 5×7 cm or similar. The element 12 is swivel-mounted in a suitable recess 13 in the lining 7 and therefore can be swiveled or moved about the vertical axis V, formed by the guide pin 14 incorporated on a suitable guide groove 15. The element 12 is spring loaded by means of a coil spring 16, i.e. innately moved from the at-rest position shown in FIG. 2, in which it can be easily swung outward. On the inner inlet surface 17 there are, for example, two rollers 18. The element 12 is thus designed as a sliding bearing component or sliding bearing.

If the couch 4 is now moved from the completely withdrawn position shown in FIG. 2 in the direction of the arrow P into the patient tunnel 3, the edge 19 strikes the inlet surface 17 or the rollers 18. In a further movement, the element 12 is immediately swiveled about the vertical axis V and moves to the closed position, shown by a broken line, in which it is completely accommodated in the recess 13. During this, the rollers 18 run on the side surface 20 of the couch, with of course a suitable element being arranged at each side of the couch. Both inlet surfaces 17 thus lie parallel to the side surfaces of the couch. This means that the gap 9, as shown still relatively large without closure pieces in FIG. 1, is extremely narrow or completely closed, depending on how far the rollers 18 project beyond the level of the inlet surface 17. This closure of the gap thus precludes a finger or similar being trapped here. Both elements 12 remain in the position abutting against the couch during the complete inward and outward movement, i.e. the gap is closed. The elements 12 snap back outward again only after the couch has again reached its fully completely withdrawn position, as shown in FIG. 2.

FIGS. 4 and 5 show a further embodiment of an element 12, that in this case is designed as a swivel lever 21. The swivel lever 21 has two lever sections 22, 23, both of which can be swiveled around a common center of rotation D and are spring loaded by a common leaf spring 24. The front lever section 22 has a striking edge 25 that has a very small radius. It is swung slightly inward, with its position being defined by a pin guide with pin 26 and groove 27, as is the position of the second lever section 23 that is defined by the pin 28 and groove 29. The front striking edges 25 of the two opposing swivel levers 21, of which only one is shown here, are arranged somewhat closer together than the width of the couch 4. Because of this, the respective couch edge 19 strikes the respective striking edge 25 and, because of the respective radii, presses the front lever section 22 outward, thus increasing the tension of the leaf spring 24. In a further inward movement, the rear lever section 23 is also swung outward in this manner. When moved much further in, see FIG. 5, both lever sections are abutting against the sides of the patient couch in sliding fashion so that here too there is absolutely no gap on either side.

Figure 6:
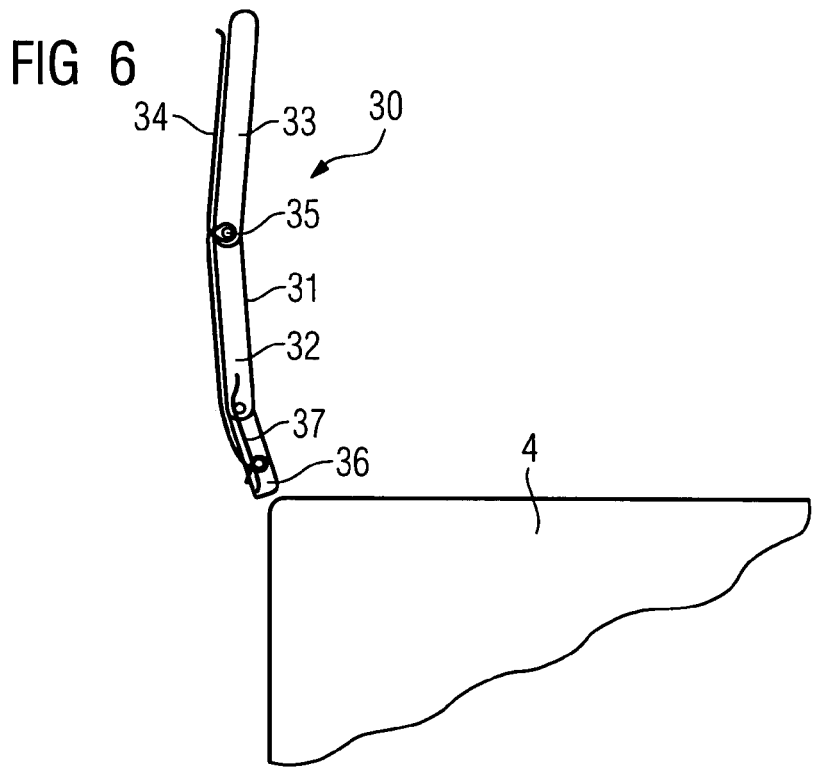

FIG. 6 shows a third embodiment of a closure element, with suitable elements here too being, of course, provided on both sides but for clarity only one side being shown. The closure element 30 shown there is also designed as a swivel lever 31, consisting of a front lever section 32 and a rear lever section 33, that here too are preloaded by a leaf spring 34 and can swivel about a common center of rotation 35. However, an extra lever section 36, which by means of a separate leaf spring 37 generates a smaller resetting force than the leaf spring 34, is provided on the front lever section 32. This foremost lever section 36 is drawn somewhat further inward, i.e. the opposite lever sections 36 are somewhat closer together than the width of the patient couch 4. Here too, both lever sections 36 are moved outward by the striking edges of the couch. Both lever sections 36 open out very easily because the leaf spring 37 generates only a slight resetting force. They are relatively short compared to the other lever sections. This results in a multi-link construction which in turn leaves absolutely no gap when the couch is moved in.

Figure 7:
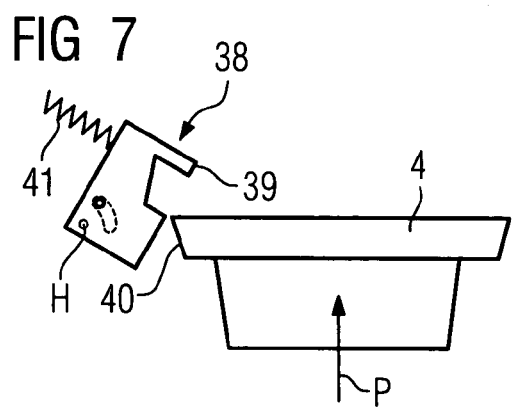
Figure 8:
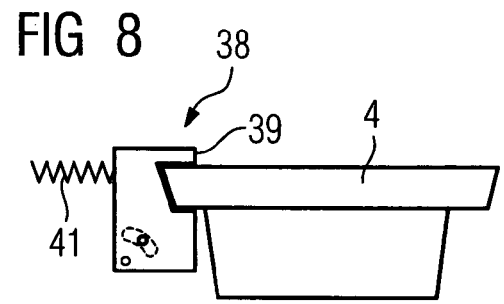

A further embodiment of an element 38 is shown in FIG. 7. The element shown there can swivel about a horizontal axis H and is designed as a type of clamp with an upper pickup section 39, against which the side edge 40 of the vertically raised patient couch 4, as shown by arrow P, strikes. In this case, both elements 38 (again in FIG. 7 only one side of one of the elements is shown) are swiveled upward about the horizontal axis H against the respective resetting force of the coil spring 41 (a leaf spring would also be conceivable in this case). In this position, see FIG. 8, the clamp-type elements 38 embrace both side edges of the couch 4. The dimensioning is arranged so that the clamp-type recess corresponds essentially to the dimensions of the respective side edge of the couch 4, so that in this case also no significant gap forms. The upper pickup section 39 in this case slides on the surface of the couch.

Figure 9:
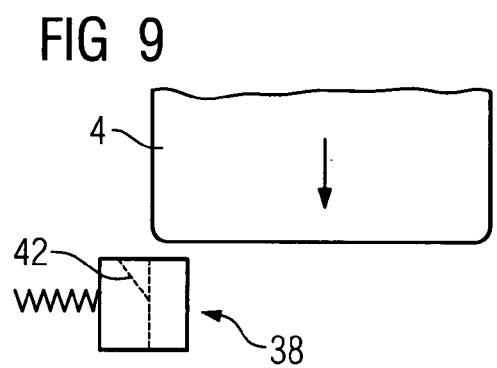

As shown in FIG. 9, there is in this case the possibility of moving the patient couch so far into the patient tunnel that the respective side edge again comes out of engagement with both elements 38. These are then, because not locked in the closed position shown in FIG. 8, again swung downward into the at-rest position by means of the respective coil spring, as shown in FIG. 7. In order to enable insertion of the relevant edges into a clamp-type element recess when moving back, an inner insertion bevel 42, only shown as a dotted line here, against which the respective couch edge runs is provided on the rear side of the elements 38. In a further movement, the respective element 38 is now raised and the edge of the couch is again inserted into the clamp-type recess.

A common feature of all embodiments is that the closure element regardless of which type is always closed when in principle there is, during the horizontal inward movement, a danger that a finger or section of skin or similar could find its way into a gap. Because of the arrangement of the elements on the front end of the lining-side recess and the fact that the elements are moved immediately by the front edges of the patient couch to the closed position, in which the gaps are largely or completely closed, there is a gap closure during virtually the complete horizontal movement of the couch.

It should be mentioned, only for completeness, that it is also conceivable to provide a sensor element 43 (see FIG. 2) that detects whether an impermissibly high pressure or impermissibly high force is acting on the respective element (here shown only in respect of element 12 from FIG. 2, but also applicable equally to each other element) or whether the element is in a specific impermissible position. If for any reason, including during the insertion of the couch into the recess (the couch is only a few millimeters distance from the recess, and consequently from the respective elements) a finger or similar should become trapped, this could be detected immediately by the sensors and an emergency stop of the couch activated via the central control device.

The invention claimed is:

1. A medical device, comprising:
   a patient tunnel lined by a lining;
   a patient couch that is moved into and out of the tunnel and accommodated in a recess in the lining enclosing sides of the patient couch; and an element that is deflected by the patient couch during a movement of the patient couch and moved against a resetting force provided at both sides in an area of an end of the recess near to the patient couch.

2. The medical device as claimed in claim 1, wherein the element is swivel mounted in the lining.

3. The medical device as claimed in claim 2, wherein the element is a sliding bearing component that swivels about a vertical axis.

4. The medical device as claimed in claim 3, wherein the sliding bearing component comprises a roller or a sliding covering on a side that engages with the patient couch.

5. The medical device as claimed in claim 3, wherein a running surface of the sliding bearing component slopes at an angle relative to a longitudinal axis of the patient couch in an at-rest position and parallels to the longitudinal axis in a swung-in position.

6. The medical device as claimed in claim 2, wherein the element is a swivel lever that swivels about a vertical axis.

7. The medical device as claimed in claim 6, wherein a rounded striking edge for the patient couch is provided on the swivel lever.

8. The medical device as claimed in claim 6, wherein the swivel lever comprises a front lever section and a rear lever section that swivel about a common center of rotation against the resetting force.

9. The medical device as claimed in claim 8, wherein the swivel lever is coupled with a leaf spring or a coil spring that generates the resetting force applied to the front and rear lever sections.

10. The medical device as claimed in claim 6, wherein the swivel lever comprises a separate further lever section that is moved against a further resetting force to be first engaged by the patient couch.

11. The medical device as claimed in claim 10, wherein the separate further lever section is arranged at an end near the patient couch.

12. The medical device as claimed in claim 2, wherein the element swivels about a horizontal axis and comprises a pickup section which engages over a top of an edge of the patient couch.

13. The medical device as claimed in claim 12, wherein the element is a clamp and engages over the top of the edge of the patient couch both sides and undersides.

14. The medical device as claimed in claim 12, wherein the element comprises a pickup bevel on a rear end for gripping the element and moving the element from an at-rest position to a swung-in position by the patient couch.

15. The medical device as claimed in claim 1, further comprising a sensor that detects an impermissibly high force acting on the element or an impermissible element position and communicates with a control device that controls the movement of the patient couch.

16. The medical device as claimed in claim 1, wherein the movement of the patient couch is a vertical movement from a lowered position into a raised completely withdrawn position or at a start of an inward movement against the resetting force to a position separated from the patient couch by a narrow gap or to a position abutting against the patient couch.

17. The medical device as claimed in claim 1, wherein the patient couch has a clearance from the lining when moved to a completely withdrawn position from the tunnel.

18. A method for reducing a risk of trapping a patient in a patient tunnel of a medical device when examining the patient by the medical device, comprising:
  lining the patient tunnel;
  supporting the patient in a patient couch;
  moving the patient couch into and out of the tunnel;
  accommodating the patient couch in a recess in the lining enclosing sides of the patient couch; and
  mounting an element in the lining that is deflected by the patient couch during a movement of the patient couch and moved against a resetting force provided at both sides in an area of an end of the recess near to the patient couch.

* * * * *